US008388592B1

(12) United States Patent  
Gentile et al.

(10) Patent No.: US 8,388,592 B1  
(45) Date of Patent: Mar. 5, 2013

(54) SANITARY PAD AND PACKAGING WITH ATTACHED BAG

(76) Inventors: Veronica Gentile, Melbourne (AU); Grace Gentile, Melbourne (AU)

( * ) Notice: Subject to any disclaimer, the term of this patent is extended or adjusted under 35 U.S.C. 154(b) by 86 days.

(21) Appl. No.: 13/020,417

(22) Filed: Feb. 3, 2011

(51) Int. Cl.  
*A61F 13/15* (2006.01)  
*A61F 13/20* (2006.01)

(52) U.S. Cl. .......... 604/385.02; 604/385.13; 604/385.19

(58) Field of Classification Search ............. 604/385.13, 604/385.19  
See application file for complete search history.

(56) References Cited

U.S. PATENT DOCUMENTS

| | | | |
|---|---|---|---|
| 4,182,336 A | 1/1980 | Black | |
| 4,556,146 A * | 12/1985 | Swanson et al. | 206/440 |
| 4,581,027 A | 4/1986 | Alvarado | |
| 4,605,403 A | 8/1986 | Tucker | |
| 4,781,712 A | 11/1988 | Barabino et al. | |
| 4,857,066 A | 8/1989 | Allison | |
| D345,210 S | 3/1994 | Thomas | |
| 2007/0049891 A1* | 3/2007 | Clark et al. | 604/385.13 |
| 2008/0077104 A1* | 3/2008 | Baer et al. | 604/385.13 |
| 2009/0105680 A1* | 4/2009 | Amiot et al. | 604/385.02 |
| 2011/0208148 A1* | 8/2011 | Chicoine et al. | 604/385.02 |

OTHER PUBLICATIONS

WWW.INPAMA.COM; SWIB sanitary napkin with integrated hygiene bag; internet; date unknown.

* cited by examiner

*Primary Examiner* — Susan Su

(57) ABSTRACT

A sanitary pad packaging system featuring a sleeve-like packaging having a top surface, a bottom surface, and an inner cavity, wherein the inner cavity is adapted to hold a sanitary pad. A first crease and second crease are disposed in the top surface of the packaging, and a third crease and fourth crease are disposed in the bottom surface of the packaging. The first crease and second crease divide the top surface into generally equal thirds, and the third crease and fourth crease divide the bottom surface into generally equal thirds. The creases allow the sleeve-like packaging to move between a folded and unfolded position. A slot disposed is in the second crease allowing access to the inner cavity of the sleeve-like packaging. A pocket is disposed on the bottom surface of the sleeve-like packaging. The pocket has an inner cavity and an open end for accessing the inner cavity.

1 Claim, 2 Drawing Sheets

SANITARY PAD AND PACKAGING WITH ATTACHED BAG

FIELD OF THE INVENTION

The present invention is directed to sanitary pads, more particularly to a sanitary pad with a packaging featuring an attached bag for sanitary disposal purposes.

BACKGROUND OF THE INVENTION

When pads are disposed of, particularly in public restrooms, users often choose to place the pads in the provided sanitary bins. However, the sticky strips of the sanitary pad can easily become stuck on the sanitary bin, creating an unhygienic disposal process. The present invention features a novel sanitary pad wrapped in packaging with an attached bag used for disposal purposes. The present invention can help improve hygiene and help prevent the spread of germs, as well as provide an easy and fast means of disposing of sanitary pads.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features a sanitary pad packaging system. In some embodiments, the system comprises a sleeve-like packaging having a top surface, a bottom surface, and an inner cavity, the inner cavity is adapted to hold a sanitary pad, wherein a first crease and a second crease are disposed in the top surface of the packaging and a third crease and a fourth crease are disposed in the bottom surface of the packaging, the first crease and second crease divide the top surface into generally equal thirds and the third crease and fourth crease divide the bottom surface into generally equal thirds, the creases allow the sleeve-like packaging to move between at least a folded position and an unfolded position; a slot disposed in the second crease, the slot allows access to the inner cavity of the sleeve-like packaging; and a pocket disposed on the bottom surface of the sleeve-like packaging at a first side edge, the pocket has an inner cavity and an open end for accessing the inner cavity.

In some embodiments, the sanitary pad packaging system further comprises a sanitary pad disposed in the inner cavity of the sleeve-like packaging.

DESCRIPTION OF PREFERRED EMBODIMENTS

Figure 1:
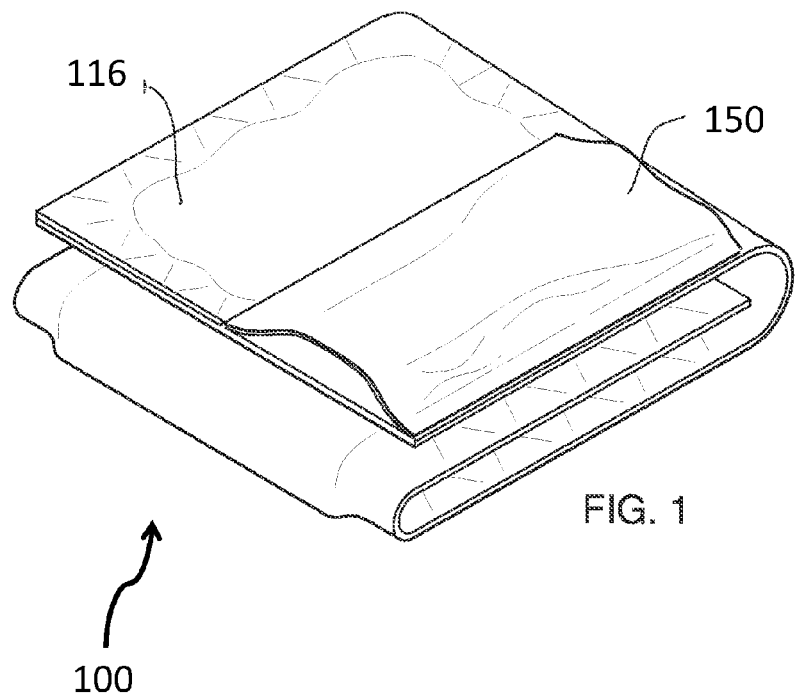
FIG. 1 is a perspective view of the sanitary pad and packaging of the present invention, wherein the sanitary pad is in the folded position.

Referring now to FIGS. 1-4, the present invention features a novel sanitary pad and packaging with an attached bag 100 used for disposal purposes. The sanitary pad 110 may be a standard sanitary pad well known to one of ordinary skill in the art. Generally, sanitary pads are elongated and have a top surface, a bottom surface, and side edges.

The packaging 120 of the present invention is a sleeve having a top surface 115, a bottom surface 116, a first side edge 210, a second side edge 220, a third side edge 230, a fourth side edge 240, and an inner cavity. The inner cavity is adapted hold the sanitary pad 110. A first crease 128a and a second crease 128b are disposed in the top surface of the packaging 120. The first crease 128a and second crease 128b may divide the top surface 115 into generally equal thirds (e.g., see FIG. 3). In some embodiments, the second crease 128b also features a slot 129 adapted to allow a user to access the pad 110 inside the packaging 120. A third crease 128c and a fourth crease 128d are both disposed in the bottom surface of the packaging 120. The third crease 128c and fourth crease 128d may divide the bottom surface 116 into generally equal thirds (e.g., see FIG. 4).

Figure 2:
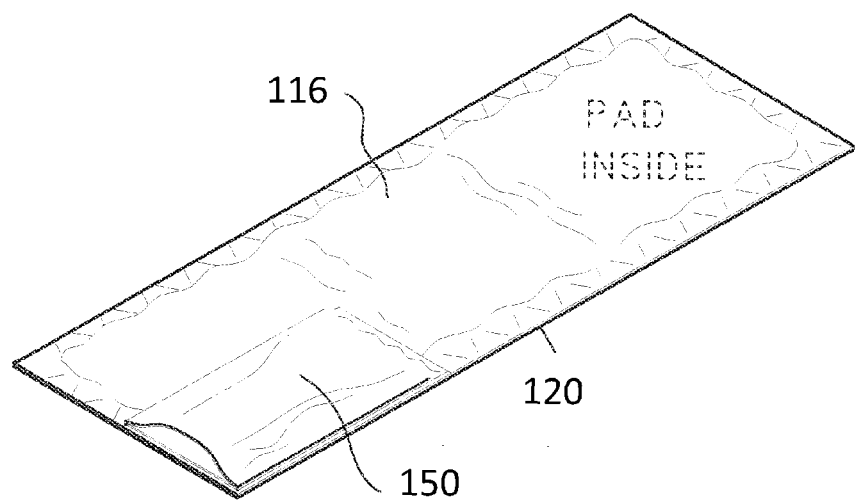
FIG. 2 is a perspective view of the sanitary pad and packaging of the present invention, wherein the sanitary pad is in the unfolded position.
Figure 3:
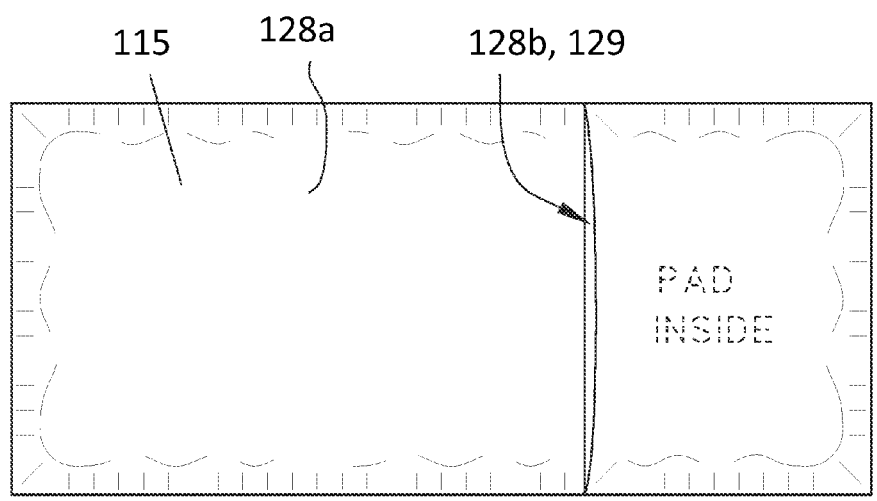
FIG. 3 is a top view of the sanitary pad and packaging of the present invention, wherein the sanitary pad is in the unfolded position.
Figure 4:
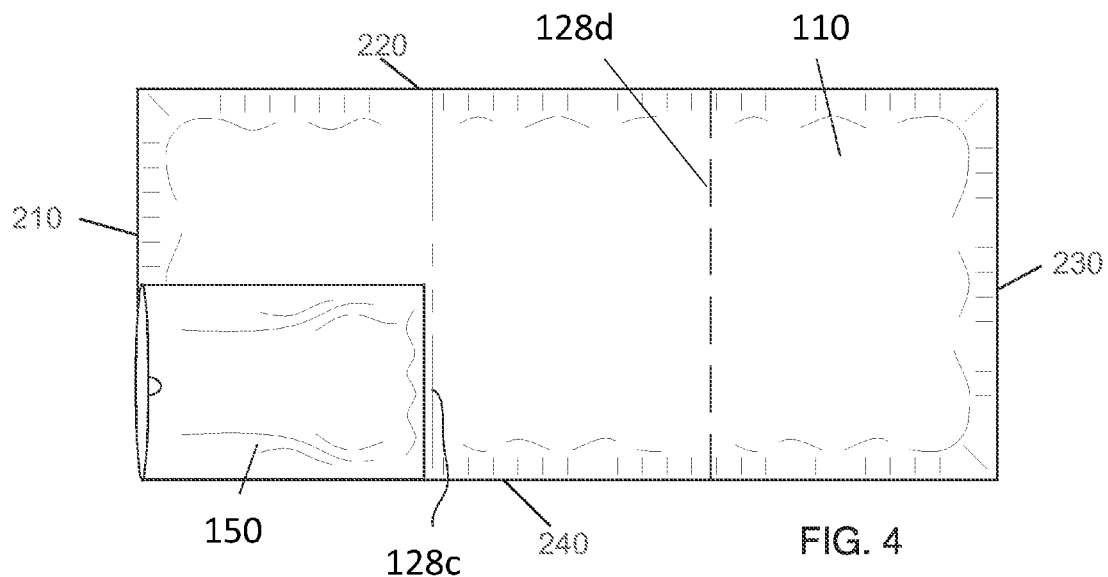
FIG. 4 is a bottom view of the sanitary pad and packaging of the present invention, wherein the sanitary pad is in the unfolded position.

The creases 128 allow the packaging 120 (and pad 110) to move between a folded and unfolded position (and optionally position in between). For example, the creases 128 divide the packaging 120 into a first portion, a middle portion, and a second portion, wherein the first portion can be folded over the middle portion and the second portion can be folded atop the first portion (the back of the first portion), for example as shown in FIG. 1. The unfolded position is shown in FIG. 2-4.

Disposed on the bottom surface 116 of the packaging 120 at the first side edge is a pocket 150. The pocket 150 is adapted to be used for disposal purposes of the sanitary pad (or another used sanitary pad). The pocket 150 has an open end for accessing the inner cavity of the pocket 150. The pocket opening side aligns with the first edge 210 and extends to third crease 128c.

The disclosures of the following U.S. Patents are incorporated in their entirety by reference herein: U.S. Pat. No. 4,605,403; U.S. Pat. No. 4,182,336; U.S. Pat. No. 4,581,027; U.S. Pat. No. 4,857,066; U.S. Pat. No. 4,781,712; U.S. Design Pat. No. D345,210.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A sanitary pad packaging system comprising:
   (a) a sleeve-like packaging (120) having four side edges in an unfolded position, a top surface (115), and a bottom surface (116), the sleeve-like packaging defining a longitudinal direction and a transverse direction, the sleeve-like packaging further has an inner cavity defined by the top and bottom surfaces, the inner cavity is adapted to hold a sanitary pad (110), wherein a first crease (128*a*) and a second crease (128*b*) are disposed in the top surface (115) in the transverse direction of the packaging (120) and a third crease (128*c*) and a fourth crease (128*d*) are disposed in the bottom surface in the transverse direction of the packaging (120), the first crease (128*a*) and second crease (128*b*) divide the top surface (115) into generally equal thirds and the third crease (128*c*) and fourth crease (128*d*) divide the bottom surface (116) into generally equal thirds, the creases (128) allow the sleeve-like packaging (120) to move between a folded position and the unfolded position;

(b) a slot (129) disposed in the second crease (128*b*), the slot (129) allows access to the inner cavity of the sleeve-like packaging (120);

(c) a pocket (150) disposed on the bottom surface (116) of the sleeve-like packaging (120) at the first side edge, the pocket (150) has an open end for accessing an inner cavity separate from the inner cavity of the sleeve-like packaging, wherein the open end extends in the transverse direction along the first side edge; and (d) a sanitary pad (110) disposed in the inner cavity of the sleeve-like packaging (120), wherein the pad is configured to be folded by folding the sleeve-like packaging at the creases and configured to be unfolded by unfolding the sleeve-like packaging.

\* \* \* \* \*